United States Patent [19]

Tsuchiya

[11] Patent Number: 4,718,761
[45] Date of Patent: Jan. 12, 1988

[54] INSTRUMENT FOR CONCURRENTLY MEASURING ULTRA-HIGH-SPEED LIGHT SIGNALS ON A PLURALITY OF CHANNELS

[75] Inventor: Yutaka Tsuchiya, Hamamatsu, Japan

[73] Assignee: Hamamatsu Photonics Kabushiki Kaisha, Hamamatsu, Japan

[21] Appl. No.: 827,067

[22] Filed: Feb. 7, 1986

[30] Foreign Application Priority Data

Feb. 8, 1985 [JP] Japan ................................. 60-22874

[51] Int. Cl.$^4$ ............................................ G01N 21/64
[52] U.S. Cl. .............................. 356/318; 250/213 VT; 250/458.1
[58] Field of Search .............. 356/218, 225, 226, 317, 356/318; 250/458.1, 459.1, 461.1, 461.2, 213 VT

[56] References Cited

U.S. PATENT DOCUMENTS

| | | | |
|---|---|---|---|
| 4,327,285 | 4/1982 | Bradley | 250/213 VT |
| 4,413,178 | 11/1983 | Mourou et al. | 250/213 VT |
| 4,461,572 | 7/1984 | Tsuchiya | 356/318 |
| 4,611,920 | 9/1986 | Tsuchiya | 356/318 |

FOREIGN PATENT DOCUMENTS 2129548 5/1984 United Kingdom ................ 356/318

OTHER PUBLICATIONS

Y. Tsuchiya et al., *Proceedings,* SPIE vol. 348, Aug. 21-27, 1982, pp. 245-250.
Y. Tsuchiya, *IEEE Journal of Quantum Electronics,* vol. QE-20, No. 12, Dec. 1984, pp. 1516-1528.

*Primary Examiner*—F. L. Evans
*Attorney, Agent, or Firm*—Spencer & Frank

[57] ABSTRACT

An instrument concurrently measuring the ultra-high-speed light signals on a plurality of channels, and consisting of a streaking tube, optical means, deflection voltage generation means, a photodiode array and processing means. It can be used to periodically measure the mechanical distortion of the object being measured when a dye laser beam pulse is incident of the object, and time-serial data is developed on a plurality of channels to output parallel data on a parallel time base.

8 Claims, 10 Drawing Figures

INSTRUMENT FOR CONCURRENTLY MEASURING ULTRA-HIGH-SPEED LIGHT SIGNALS ON A PLURALITY OF CHANNELS

BACKGROUND OF THE INVENTION

The present invention relates to in instrument for measuring two-dimensional light images which are repeated at ultra-high speed, and especially to an instrument for concurrently measuring two-dimensional multichannel light images which may change at ultra-high speed, i.e., the time-resolving spectroscopic measurement of fluorescence stimulated by a laser pulse, or spatial time-resolving measurements in the pico second range.

The streaking camera is used as an instrument to observe an optical intensity distribution changing at high speed.

The streaking tube used in the streak camera is an electron tube wherein a pair of deflection electrodes are arranged in a space between the photocathode and phosphor layer.

When the light pulse in incident on the photocathode of the streaking tube, the photocathode emits photoelectrons.

If an electric field is applied across the pair of deflection electrodes while the photoelectrons move toward the phosphor layer, the incident light intensity change can be detected on the phosphor layer as a linear light intensity distribution along the sweeping trace on the phosphor screen (in the direction of scanning with time).

This light intensity distribution is called a streaking image.

The streak camera consists of a streaking tube, an optical system to project the light pulse to be measured onto the photocathode of the streaking tube, and a power supply to feed the supply voltage to the streaking tube.

High-repetition-rate pulse light measuring instruments (Japanese Patent Application Laid-Open Nos. 104519/1984 and 135330/1984) and an electron tube device for the high-repetition-rate pulse light measuring instruments (Japanese Patent Application Laid-Open No. 134538/1984) have already been proposed, and these instruments and device apply to the light emitted at high repetition rate in accordance with the principle of operation of the streaking tube aforementioned.

These are suitable for measuring the extremely low intensity light changing with time at a high repetition rate. Data arranged on the streaking tube in a direction perpendicular to the sweeping of the streaking tube cannot be output at the same time. That is, data on a plurality of channels cannot be output concurrently.

The streaking image on the phosphor layer of the streaking tube can be analyzed by picking it up on the television camera.

Highly repetitive streak images can be superimposed during one frame time (1/30 or 1/60 sec.) and this is picked up by the television camera. Therefore, an image signal with greater level can be obtained.

The dynamic range, however, is limited to a value much lower than $10^4$ to $10^6$ because of the following four reasons:

First, the image is stored as charges in the target capacitance of the pick up tube and the dynamic range of an image for one field period is of the order of 100 to 1.

Second, charges caused by the dark current of the pick up tube are stored during the above one field and the measurement accuracy of faint streaking images is low.

Third, the dynamic range of the streaking image for a plurality of fields is also limited to 1000:1 by both the target capacitance and dark current.

The dynamic range of the streaking image can be improved by feeding the streaking tube output to a photomultiplier tube when such an electron tube device for measuring the high-speed light pulses as disclosed in Japanese Patent Application Laid-Open No. 134538/1984 is used. The streaking images on a plurality of channels, however, cannot concurrently be measured.

The streaking images on a plurality of channels can only be measured in sequence, and this lengthens the measuring time.

The objective of the present invention is to provide an instrument for measuring a two-dimensional light image repetitively appearing at ultra-high speed, i.e., an instrument for the time-resolving spectroscopic measurement of fluorescence stimulated by a laser pulse, or an instrument for spatial time-resolving measurements in the pico second region.

SUMMARY OF THE INVENTION

An instrument to concurrently measure ultra-high-speed optical phenomena on a plurality of channels in accordance with the present invention consists of a streaking tube wherein an electron image corresponding to the optical image formed on the photocathode is deflected by a deflection field and the deflected electron beam is projected onto the phosphor layer passing through the slit plate with a slit arranged in a direction perpendicular to the direction of deflection; optical means to project the repetitive light emission from the sample onto the photocathode of the streaking tube in a direction perpendicular to the deflection; deflection voltage generation means to generate a series of deflection voltages whose phases change every light emission synchronizing with the light emission of the sample; a photodiode array consisting of photodiodes arranged on the phosphor layer of the streaking tube in a direction perpendicular to the deflection and processing means to process the output signals of the photodiode array.

EMBODIMENTS OF THE INVENTION

Figure 1:
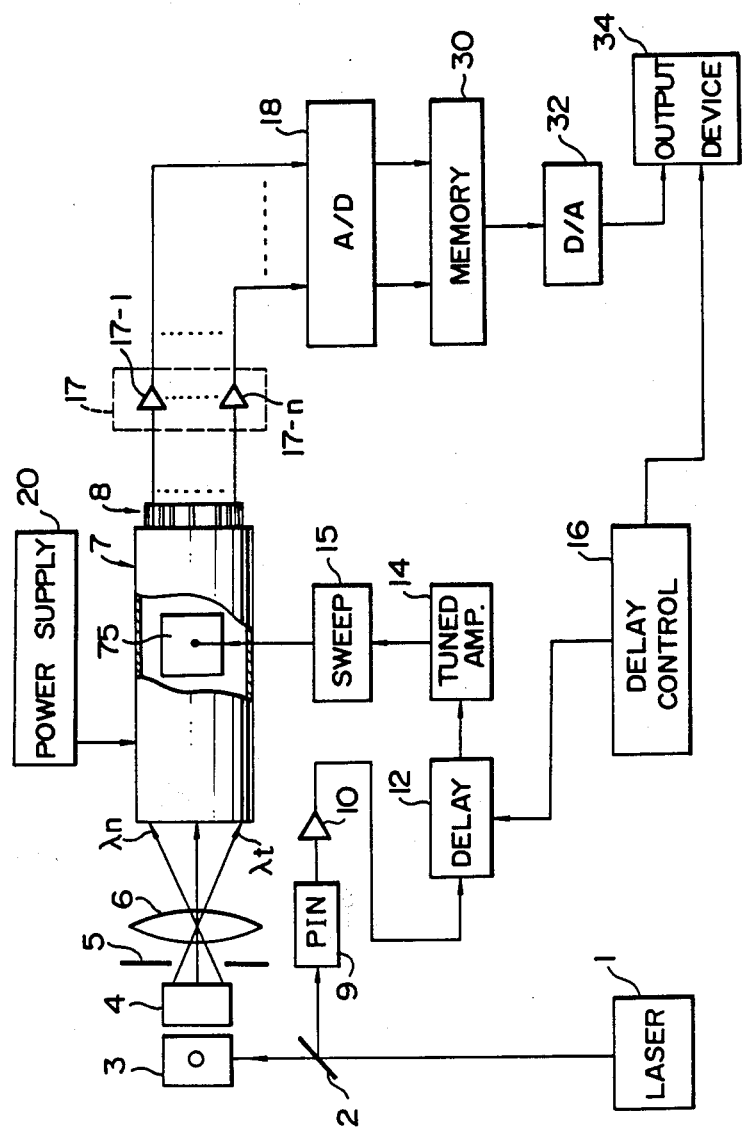
FIG. 1 is a block diagram of the first embodiment of the instrument to concurrently measure the ultra-high-speed streaking images on a plurality of channels according to the present invention.

The present invention will be described hereafter referring to the drawings.

FIG. 1 shows a block diagram of the first embodiment of the instrument for concurrently measuring the ultra-high-speed streaking images on a plurality of channels according to the present invention.

The sample set on the measuring instrument is periodically stimulated by a laser, and then light emission by fluorescence can occur in the sample. The light is spectroscopically measured.

Dye laser source 1 generates a repetitive pulse train. The repetitive pulse train branches into two paths in half mirror 2 and the light beam passing through half mirror 2 irradiates object 3. A light pulse train is generated from object 3 corresponding to the light pulse train. The light beam obtained by periodic light emission is projected onto the photocathode of the streaking tube in a direction perpendicular to the sweeping.

The optical means in the embodiment consists of spectroscope 4, slit 5 to pass the light beam components analyzed by spectroscope 4 and lens 6.

If some means to accomplish the same function are built in spectroscope 4, no independent slit plate is required.

Assume that the light beam obtained by periodical light emission is fed to the spectroscope in a pin-hole-like structure, and that the incident light beam is projected onto the photocathode of the streaking tube in a direction perpendicular to the sweeping. The slit 5 and lens 6 then become unnecessary.

The linear images in FIG. 1, formed in the plane of the drawing, contain wavelength components $\lambda 1, \lambda 2, \ldots \lambda n$ from bottom to top.

Figure 2:
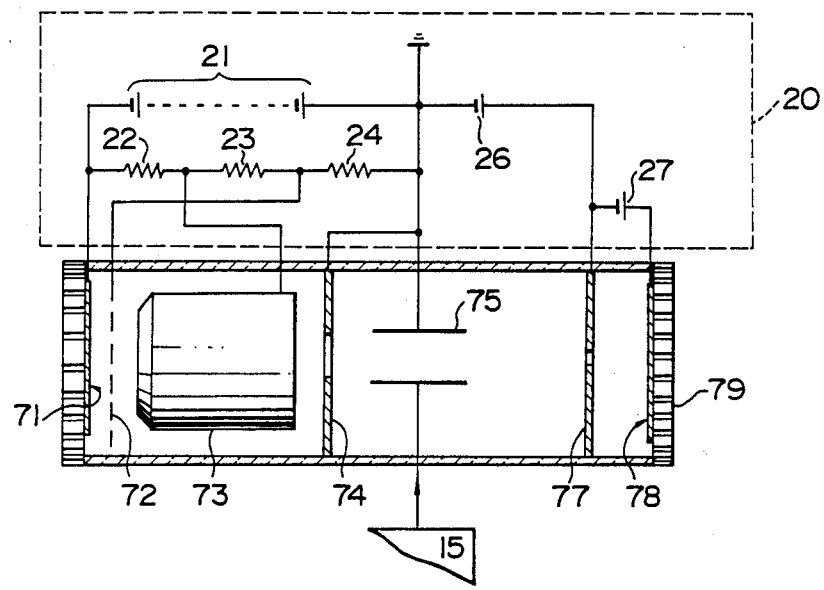
FIG. 2 is a cross-sectional view of the streaking tube used in the first embodiment of the instrument to concurrently measure the ultra-high-speed streaking images on a plurality of channels, and the circuit diagram of the power supply for the streaking tube.

FIG. 2 shows a cross-sectional view of the streaking tube used in the instrument to concurrently measure the ultra-high-speed streaking images on a plurality of channels, and the circuit diagram of the power supply for the streaking tube.

The cross-section of streaking tube 7, including the optical axis thereof, is shown in a direction perpendicular to the plane of the drawing.

Figure 3:
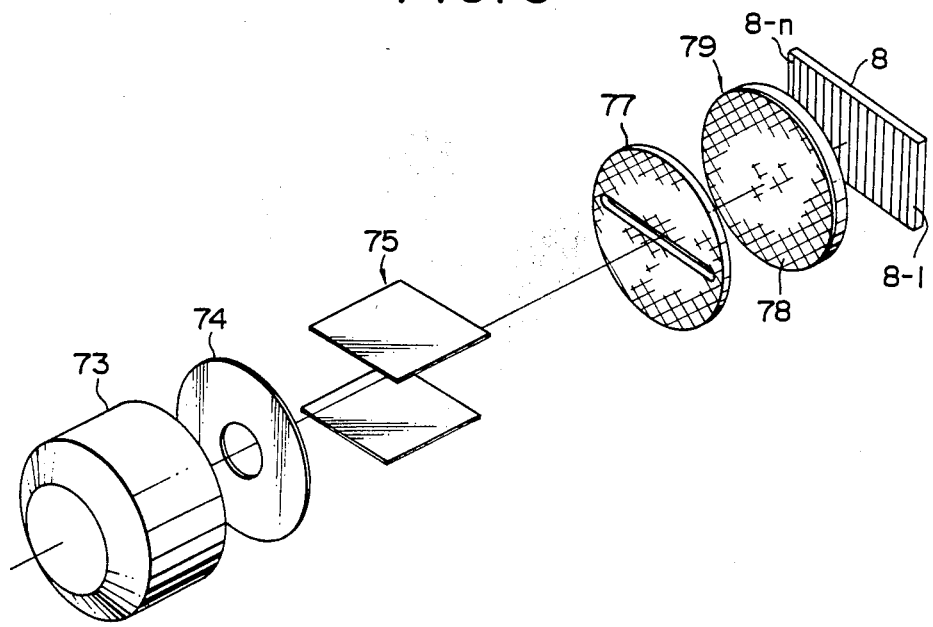
FIG. 3 is an exploded view of the electrodes arranged in the streaking tube and the photodiode array.

FIG. 3 shows an exploded view of the electrodes arranged in the streaking tube and the photodiode array.

Photocathode 71 is formed on the inner surface of the faceplate of streaking tube 7.

Mesh electrodes 72 are arranged against photocathode 71. Electrons accelerated by mesh electrodes 72 are focused by focusing electrode 73 and incident on the electric field formed by deflection electrode 75 passing through aperture plate 74.

A sweep voltage synchronizing with the light pulse caused by light emission of fluorescence is applied to deflection electrode 75. Synchronization will be described hereinafter.

Electrons deflected by deflection electrode 75 are incident on phosphor layer 78 formed on the inner surface of fiberplate 79 through slit plate 77.

The slit of slit plate 77 in FIG. 3 is perpendicular to the direction of the deflection in streaking tube 7. The operating voltages are fed from power supply 20 and sweep voltage generator 15 to the respective electrodes of streaking tube 7. The sweep voltage will be described later.

Power supply 20 consists of power regulators 21, 26 and 27, and voltage dividers 22, 23 and 24. An acceleration voltage of 3 kV to 5 kV from power supply 27 is applied across the space between slit plate 77 and phosphor layer 78.

Part of the light pulse train from dye laser pulse source 1, reflected from half mirror 2, is detected in PIN photodiode 9, amplified with amplifier 10, and then fed to tuned amplifier 14 through delay circuit 12.

The delay time in delay circuit 12 is controlled by using delay control circuit 16.

Tuned amplifier 14 is used to generate a sine-wave signal voltage tuned to the tuned pulse signal and the sine-wave signal voltage is amplified with sweep voltage generator 15. The amplified signal voltage is fed to a pair of deflection electrodes.

The linear range of the sine-wave signal voltage can be used to generate the sweep signal.

The deflection voltages and electrons arriving at the phosphor layer will be described referring to FIGS. 4 and 5.

Figure 4:
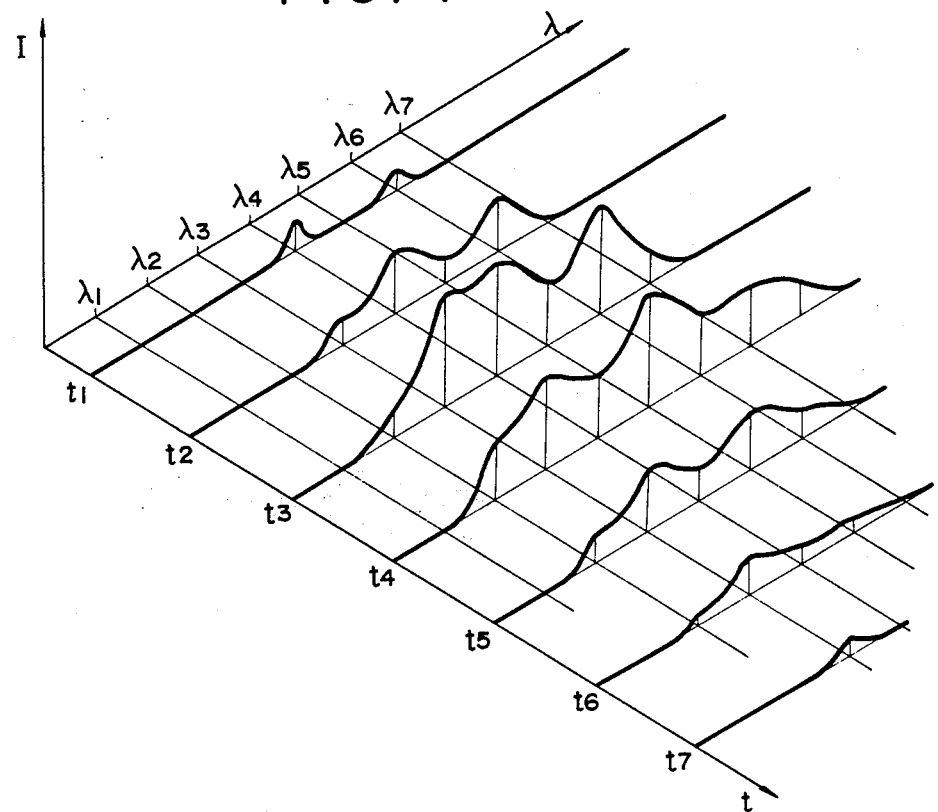
FIG. 4 shows the waveforms illustrating the change of the intensity of a single light pulse picked up from the repetitive light emission consisting of a plurality of wavelength components to be measured by the embodiment of the measuring instrument.

FIG. 4 shows the waveforms illustrating the change of the intensity of a single light pulse picked up from the repetitive light emission consisting of a plurality of wavelength components to be measured by the embodiment of the measuring instrument.

In FIG. 4, the time axis is t, the wavelength axis, is $\lambda$, and the intensity axis is I, the graph being represented in a three-dimensional space.

The $\lambda 4$ and $\lambda 6$ wavelength components, which are bound by the relation in FIG. 4, are incident on the photocathode of the streaking tube at a time of t1. The $\lambda 3$ through $\lambda 6$ wavelength components, which are bound by the relation in FIG. 4, are incident on the photocathode of the streaking tube at a time of t2.

Figure 5:
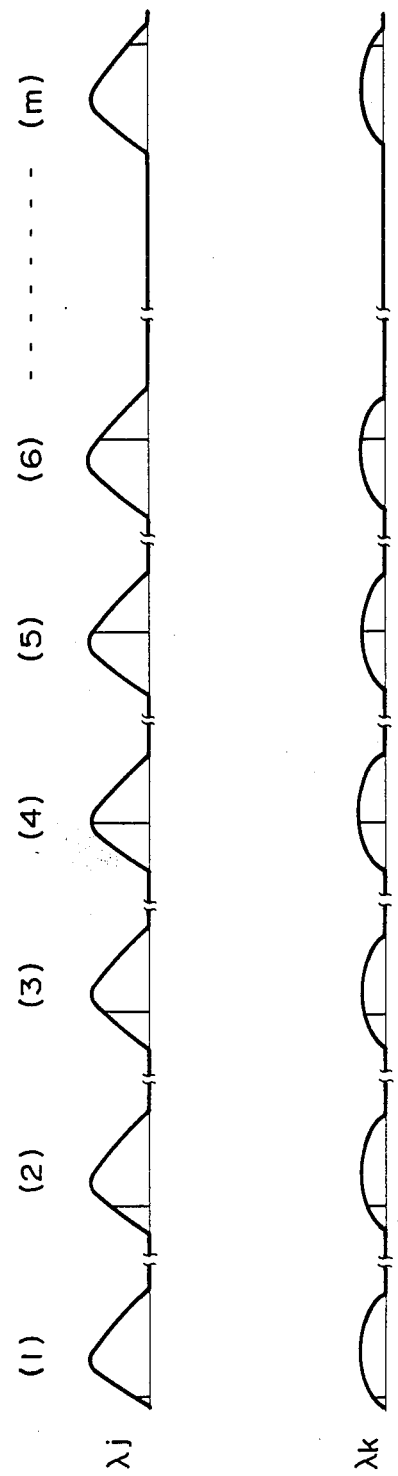
FIG. 5 shows the waveforms illustrating repetitive light emission and sampling.

FIG. 5 shows waveforms illustrating repetitive light emission and sampling.

(1) through (M) in FIG. 5 show the waveforms of the light pulses, due to light emission of fluorescence, which are incident on photocathode 71 of streaking tube 7 in the first through m-th time slots.

The light pulses due to light emission by fluorescence are analyzed by spectroscope 4, and the location on photocathode 71 where the light beam is incident depends on the wavelength of the light pulse.

λj and λk represent the light beam intensities at locations j and k of photocathode 71. Sweep voltage generator 15 generates, from electrons generated by incidence of the light beam, such a sweep signal voltage that the black stripe portion is sensed by the slit plate 77.

Photodiode array 8 consists of a number of photodiodes arranged to form a linear array in a direction perpendicular to the sweeping of streaking tube 7.

A single photodiode, having an appropriate size which can be specified in accordance with the objectives, is 100 μm×5 mm in dimensions.

Each photodiode is arranged corresponding to the specific wavelength by light emission on phosphor layer 78. Each photodiode output is amplified with each amplifier in amplifier group 17.

The output of each amplifier in amplifier group 17 is converted into the corresponding digital signal by using each A/D converter in A/D converter group 18.

The output, of each A/D converter in A/D converter group 18 is stored in a memory 30.

Information indicated by the black stripe of each incident wavelength component of light emission in the first time slot, information indicated by the black stripe of each incident wavelength component of light emission in the second time slot, and finally information indicated by the black stripe of each incident wavelength component of light emission in the m-th time slot can be stored in memory 30.

The outputs of A/D converter group 18, picked up in the first through m-th time slots, are summed together to construct a waveform due to light emission of fluorescence in the respective wavelength components.

The contents of memory 30 are read out to convert them into the corresponding time-serial analog signal by using D/A converter 32, and then the obtained analog signal is output from output device 34, i.e., VDT, synchronizing with the output of delay controller 16. Then, the output signal can be observed in real time.

Figure 6:
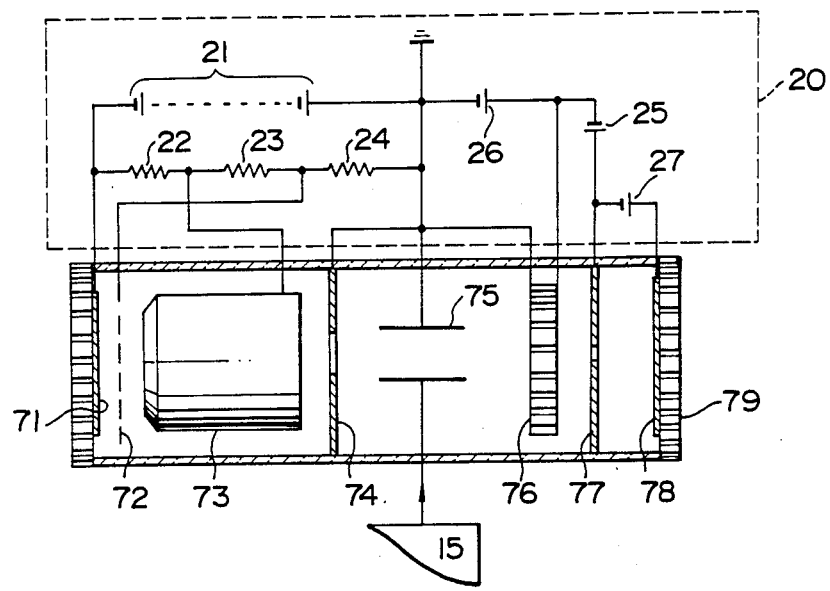
FIG. 6 shows a cross-sectional diagram of another streaking tube used in the instrument to concurrently measure the ultra-high-speed light signals on a plurality of channels, and the circuit diagram of the power supply for the streaking tube.

FIG. 6 shows the cross-sectional diagram of another streaking tube used in the instrument to concurrently measure the ultra-high-speed light signals on a plurality of channels, and the circuit diagram of the power supply for the streaking tube.

The streaking tube in FIG. 6 provides a microchannel plate 76 between deflection electrode 75 and slit plate 77 of the former streaking tube in FIG. 2 or 3 so that the multiplied photoelectrons are incident on phosphor layer 78.

Power supply 26 is used to supply the operating voltage to microchannel plate 76, power supply 25 is used to generate an acceleration field between microchannel plate 76 and slit plate 77, and power supply 27 is used to generate an acceleration field between slit 77 and phosphor layer 78. The streaking tube of this type can be used to construct the instrument to concurrently measure the ultra-high-speed light signals on a plurality of channels.

Figure 7:
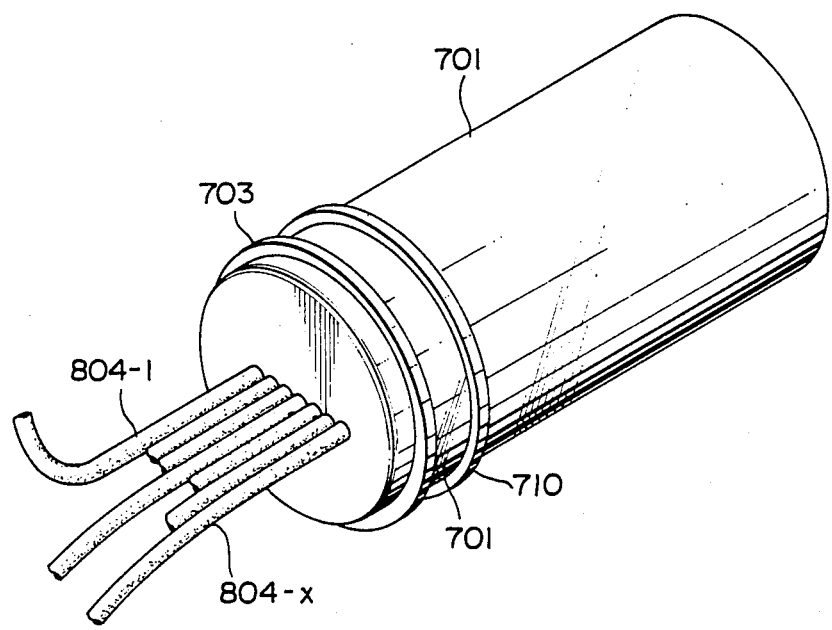
FIG. 7 shows a perspective view of a further streaking tube used in the instrument to concurrently measure the ultra-high-speed light signals on a plurality of channels, and optical means to project the streasking image on the streaking tube in a direction perpendicular to the sweeping.

FIG. 7 shows a perspective view of a further streaking tube used in the instrument to concurrenly measure the ultra-high-speed light signals on a plurality of channels according to the present invention, and optical means to project the streaking image on the streaking tube in a direction perpendicular to the sweeping.

Figure 8:
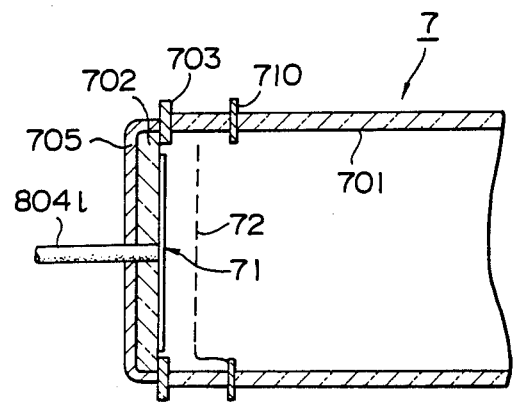
FIG. 8 shows a cross-sectional view of optical means for the streaking tube shown in FIG. 7, and the cross-sectional view of the joint portion between the optical means and the photocathode.

FIG. 8 shows a cross-sectional view of optical means for the streaking tube shown in FIG. 7, and the cross-sectional view of the joint portion between the optical means and the photocathode.

Fibers 804--1 through 804--x are fastened to the internal portions along the center line of the faceplate whereon photocathode 71 can be formed and they extend beyond the faceplate. The light beam is incident on the outer edge of each fiber and optical means are used to project the linear light beam image in a direction perpendicular to the deflection.

A glass plate is used to construct faceplate 702.

Faceplate 702 made of Kovar glass is fastened to main glass cylinder 701 via ring 703 which can also be used as a metal electrode.

Optical fibers 804--1 through 804--x are buried in faceplate 702 in a line at the center thereof.

The inner edges of optical fibers 804-1 through 804-x are set on the inner surface of faceplate 702 made of Kovar glass, and photocathode 71 is formed on the inner surface thereof.

Each of optical fibers 804-1 through 804-x consists of a clad and a core formed within the clad, and the clad is 125 μm to 200 μm in diameter.

First, faceplate 702 made of Kovar glass is cut into two segments along the diameter and then optical fibers 804-1 through 804-x can be buried.

Grooves are formed at the linear edges of two segments to set the fibers thereat.

The circumference of each fiber is placed on the groove formed at the linear edge of each segment, and each fiber is placed between a pair of grooves in a pair of segments. Glass powder is then laid on the junction between the fiber and grooves, and it is heated together with the fiber and faceplate segments so as to join them together.

After the fibers and faceplate segments are joined together, the inner surface whereon the photocathode can be formed is polished.

Photocathode 71 is formed on the inner surface of faceplate 702 and mesh electrode 72 is provided facing photocathode 71.

Aside from projections of the fibers 804-1 through 804-x from faceplate 702, shielding layer 705 of black paint is formed on part of faceplate 702 so that the light beams from any other portions than fibers 804-1 through 804-x are blocked.

The outer edges of the optical fibers 804-1 through 804-x are arranged in such locations that the periodic light signals of light emission can be received from the sample, and then the light signals of light emission in a plurality of locations can be measured concurrently.

Diodes in photodiode array 8 are related (in one-to-one correspondence) to optical fibers 804-1 through 804-x, respectively.

The faceplate of the streaking tube is divided into two sections to form a pair of grooves for connecting the fibers and faceplate. The faceplate can be made by another method. In this other method, holes are bored through the faceplate by using a diamond drill, the fibers are set in the holes, and the fibers are fastened by glass powder.

The fiber plate can be used as the faceplate.

A shielding slit plate made of aluminum, having a slit with a slit width narrower than the fiber core diameter, may be formed in front of photocathode 71 and then photocathode 71 may be formed.

The optical fibers and faceplate of the streaking tube are assembled together, and alignment of the photocathode to the fibers is unnecessary. This simplifies operation and facilitates maintenance including replacement of the streaking tube.

Figure 9:
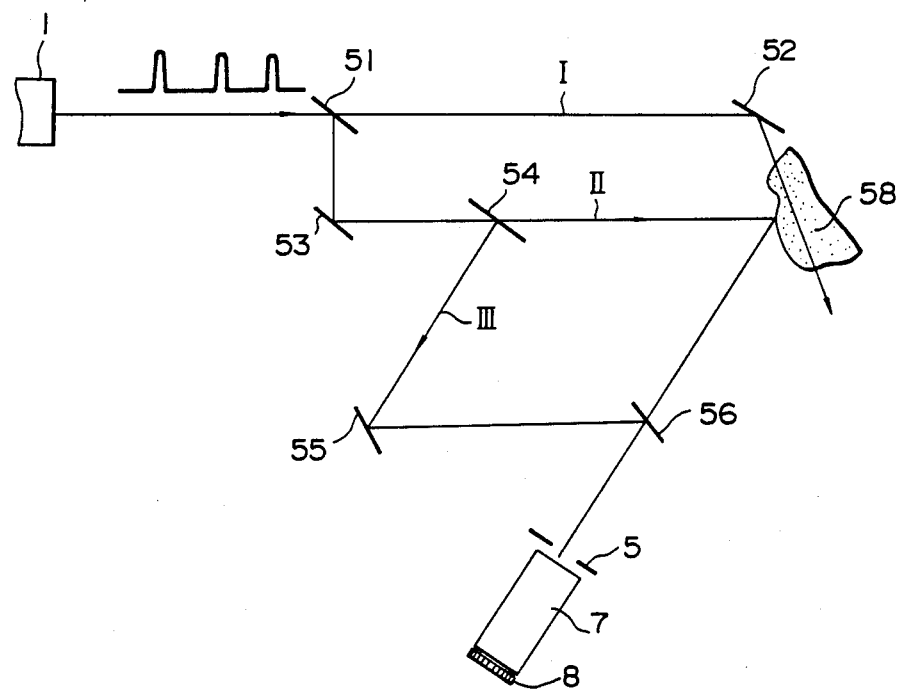
FIG. 9 shows the arrangement of optical means in the second embodiment of the instrument to concurrently measure the ultra-high-speed light signals on a plurality of channels in accordance with the present invention.

FIG. 9 shows the arrangement of optical means in the second embodiment of the instrument to concurrently measure the ultra-high-speed light signals on a plurality of channels in accordance with the present invention.

Figure 10:
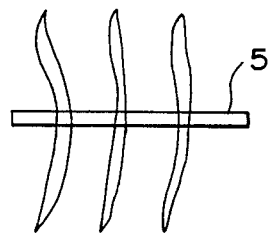
FIG. 10 is a sketch of an interference fringe which has occurred in the object being measured by the second embodiment of the instrument in accordance with the present invention.

FIG. 10 is a sketch of an interference fringe which has occurred in the object being measured by the second embodiment of the instrument in accordance with the present invention.

When a material is stimulated by laser pulse, the excited material is distorted in accordance with the excitation.

The interference fringe due to this type of distortion can be used to observe the change of the interference fringe with time.

An instrument of this type can be used to measure the ultra-high-speed displacement and the analysis of vibration.

A light pulse train from laser pulse light source 1 branches into excitation light pulse I and other light pulse when passing through half mirror 51.

Excitation light pulse I reflects from total reflection mirror 52 and the light pulse reflected from the total reflection mirror 52 stimulates material 58.

The other light pulse sent from half mirror 51 branches into exposure light pulse II and reference light pulse III when passing through half mirror 54.

The light pulse signal reflected from the surface of material 58 when the material 58 is exposed to exposure light pulse II, and the reference light pulse III are combined by using half mirror 56 so as to form an interference image corresponding to the structure of the material surface.

FIG. 10 shows an example of the interference image.

Slit plate 5 is arranged in front of streaking tube 7 and part of an interference fringe is projected onto the photocathode of streaking tube 7 so as to form a linear image thereof when the light beam passes through the slit plate 5.

Photodiode array 8 and succeeding stages, and the sweep voltage generator are the same as those of the first embodiment of the present invention.

The material structure is distorted when exposed to the laser pulse beam, and thus the material surface is displaced a little.

The memory stores the change of the structure with time.

The instruments described heretofore in detail can partly be modified within the scope of the present invention.

For instance, the mesh electrode to accelerate electrons emitted from the photocathode may be a planar electrode with a slit-like aperture.

As described above, an instrument for concurrently measuring ultra-high-speed light signals on a plurality of channels in accordance with the present invention consists of a streaking tube wherein a slit plate with a slit is arranged succeeding the deflection electrodes in such a manner that the slit is arranged in a direction perpendicular to the deflection carried out by the deflection electrodes; optical means whereby the periodical light pulse signal sent from the sample is developed and incident on the photocathode of the streaking tube in a direction perpendicular to the deflection; deflection voltage generation means to generate a series of deflection voltages whose phases are shifted a little each time scintillation has occurred while operated synchronizing with the scintillation of the sample; and a photodiode array used to pick up in parallel a series of streaking images obtained by the scintillation. Thus, the instrument built in accordance with the present invention can concurrently measure the ultra-high-speed light signals on a plurality of channels.

The size of each diode in a photodiode array can be set arbitrarily.

No scanning circuit is required to read out the streaking images because the streaking images are read out in parallel and this leads to high speed processing of data read out of the instrument.

If serial read-out operations are carried out, a shift register or a demultiplexer is needed and this makes the circuit configuration complicated.

Such linesensors as Reticon ® and CCD photosensors, which are available on the market, are not used but a diode array is used in the present invention. This results in the following features:

Spikes, Noises and Dynamic Range

Parallel read-out operations eliminate spikes and reduce noise; then this leads to high S/N value and high dynamic range.

Noise is mainly caused by amplifiers and the S/N value for a diode array is $n^{\frac{1}{2}}$ times greater than the scanned sensor. ('n' indicates the number of picture elements.)

The minimum signal level which can be read out of the sensor is limited by spikes. The diode array completely eliminates spikes, and the minimum signal level of the diode array is extended to a value limited by the amplifier noise or photocurrent shot noise.

Readout Time

Assume that n=100. The line sensor requires a read out time of 't/n' for each element, and the diode array requires 't' because data is read out in parallel from all diode array elements. The frequency bandwidths for the former and latter are 'n/(2t)' and '1/(2t)', respectively. The bandwidth for the diode array is n-times greater than that for the linear sensor.

Others

The photodiode array used in the present invention permits a readout operation in specific picture elements, and also permits a variable readout operation.

The linear array sensor has an upper bound to the scanning frequency. The scanning frequency is limited by the shift register performance. The shift register limits the readout time to 100 ns. The diode array uses amplifiers arranged in parallel with the respective diode outputs, and this reduces the sampling time to 100 ns/'n'. This reduces the equivalent amplifier bandwidth.

The sampling can be done at a speed n-times faster than that of the line sensor.

What is claimed is:

1. An instrument for receiving repetitive ultra-high-speed light signals from a sample and concurrently measuring said light signals on a plurality of channels, comprising:

optical means for projecting said repetitive light signals in a first direction;

a streaking tube including
  a photocathode for receiving the light signals projected by said optical means and generating an electron image corresponding thereto;
  a phosphor layer spaced from said photocathode;
  deflection electrodes interposed between said photocathode and said phosphor layer, said deflection electrodes sweeping electrons forming said electron image in a second direction perpendicular to said first direction; and a first slit plate having a first slit therein interposed between said deflection electrodes and said phosphor layer, said first slit extending in said first direction;

deflection voltage generation means coupled to said deflection electrodes, said voltage generation means generating a series of deflection voltages which are synchronized with the light signals from said sample and whose phases are shifted slightly each time a repetitive light signal is received at said photocathode;

a photodiode array arranged adjacent and facing said phosphor layer, said photodiode array comprising a plurality of photodiodes extending in said first direction; and processing means for processing the outputs of said photodiode array.

2. An instrument as claimed in claim 1 which further comprises a laser device, said laser device emitting a laser pulse beam for exciting said sample, whereby said repetitive light signals are emitted by said sample.

3. An instrument as claimed in claim 2, wherein said laser device is a dye laser device operated at a relatively high repetition rate.

4. An instrument as claimed in claim 1, wherein said optical means comprises:

a spectroscope for analyzing the light signals emitted by said sample due to the excitation thereof;

a second slit plate having a second slit therein extending in said first direction, said second slit plate being in the path of light emitted by said spectroscope; and optics for forming images of the light signals passing through said second slit plate onto the photocathode of said streaking tube.

5. An instrument as claimed in claim 1, wherein said optical means comprises an optical element for feeding said light signals due to excitation of said sample to a spectroscope through a pin hole, said spectroscope projecting the light signals fed through said pin hole onto said photocathode of said streaking tube in said first direction.

6. An instrument as claimed in claim 1, wherein said streaking tube further comprises a faceplate to which said photocathode is affixed, and wherein said optical means comprises a plurality of fibers for receiving said light signals due to scintillation of said sample in a plurality of locations on said faceplate.

7. An instrument as claimed in claim 1, wherein said repetitive light signals are produced by periodic displacement of said sample; and said optical means comprises a laser device for periodically generating light pulses;

an excitation light path for irradiating the light pulses emitted by said laser device and impinging on said sample so as to excite said sample;

an exposure light path for exposing the surface of said sample to the light pulses emitted by said laser device;

a reference light path for leading a reference light for interference with light reflected from said sample passing through said exposure light path, said reference light being incident on said streaking tube, and slit means for joining an interference fringe pattern formed by the interference between said exposure light and said reference light to the photocathode of said streaking tube thereby forming a linear image in said first direction.

8. An instrument as claimed in claim 1, wherein said optical means comprises:

a spectroscope for analyzing the light signals emitted by said sample due to the excitation thereof, said spectroscope having;

a second slit therein extending in said first direction; and optics for forming images of the light signals passing through said second slit onto the photocathode of said streaking tube.

* * * * *